US005695977A

United States Patent [19]
Jurka

[11] Patent Number: 5,695,977
[45] Date of Patent: Dec. 9, 1997

[54] SITE DIRECTED RECOMBINATION

[75] Inventor: Jerzy W. Jurka, Los Altos, Calif.

[73] Assignee: Genetic Information Research Institute, Palo Alto, Calif.

[21] Appl. No.: 643,886

[22] Filed: May 7, 1996

Related U.S. Application Data

[60] Provisional application No. 60/003,063, Aug. 31, 1995.
[51] Int. Cl.[6] ............................ C12N 15/09; C07H 21/04
[52] U.S. Cl. ...................... 435/172.3; 536/23.1; 536/24.5
[58] Field of Search ........................... 435/172.3; 935/52; 536/23.1, 24.5

[56] References Cited

U.S. PATENT DOCUMENTS 5,292,662  3/1994  Sandmeyer ........................... 435/320.1

OTHER PUBLICATIONS

*Ann. Rev. Biochem.* 1986. 55:631–61, Copyright 1986; Alan M. Weiner, Prescott L. Deiniger, Argiris Efstratiadis, "Non-viral Retroposons: Genes, Pseudogenes, and Transposable Elements Generated by the Reverse Flow of Genetic Information".

*Proc. Natl. Acad. Sci. USA,* vol.91, pp. 6064–6068, Jun. 1994, Biochemistry; Philippe Rouet, Fatima Smih, Maria Jasin, "Expression of a site–specific endonuclease stimulates homologous recombination in mammalian cells".

*The EMBO Journal,* vol.2, No. 5 pp.757–761, 1983; Marion Moos, Dieter Gallwitz, "Structure of two human β–actin–related processed genes one of which is located next to a simple repetitive sequence".

*Proc. Natl. Acad. Sci. USA,* vol.92, pp.806–810, Jan. 1995, Biochemistry; David J. Segal, Dana Carroll, "Endonuclease–induced, targeted homologous extrachromosomal recombination in Xenopus oocytes".

*Nucleic Acids Research,* vol. 13, No. 24, 1985, Gary R. Daniels, Prescott L. Deininger, "Integration site preferences of the Alu family and similar repetitive DNA sequences".

*Cell,* vol. 26, 11–17, Oct. 1981 (Part 1), Copyright 1981; Scott W. Van Arsdell, Richard A. Denison, Laurel B. Bernstein, Alan M. Weiner, "Direct Repeats Flank Three Small Nuclear RNA Pseudogenes in the Human Genome".

*The EMBO Journal,* vol. 14, No. 24, pp.6333–6338, 1985; Joel Maestre, Thierry Tchenio, Olivier Dhellin, Thierry Heidmann, "mRNA retroposition in human cells: processed pseudogene formation".

*Primary Examiner*—George C. Elliott
*Assistant Examiner*—Robert Schwartzman
*Attorney, Agent, or Firm*—Flehr Hohbach Test Albritton & Herbert, LLP

[57] ABSTRACT

Enhanced homologous recombination is obtained by employing a consensus sequence which has been found to be associated with integration of repeat sequences, such as Alu and ID. The consensus sequence or sequence having a single transition mutation determines one site of a double break which allows for high efficiency of integration at the site. By introducing single or double stranded DNA having the consensus sequence flanking region joined to a sequence of interest, one can reproducibly direct integration of the sequence of interest at one or a limited number of sites. In this way, specific sites can be identified and homologous recombination achieved at the site by employing a second flanking sequence associated with a sequence proximal to the 3'-nick.

17 Claims, No Drawings

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="sequence"

( x i ) SEQUENCE DESCRIPTION: SEQ ID NO:1:

TTAAANYYYN 10

( 2 ) INFORMATION FOR SEQ ID NO:2:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="sequence"

( x i ) SEQUENCE DESCRIPTION: SEQ ID NO:2:

TTAAAANNYY YN 12

( 2 ) INFORMATION FOR SEQ ID NO:3:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="sequence"

( x i ) SEQUENCE DESCRIPTION: SEQ ID NO:3:

TTAAAANNNY YYN 13

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:4:

TTAAAANNNN YYYN 14

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:5:

TTAAAANNNN NYYYN 15

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:6:

TTAAAANNNN NNYYYN 16

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:7:

TTAAAANNNN NNNYYYN 17

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:8:

TTAAAANNNN NNNNYYYN 18

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="sequence"

(xi) SEQUENCE DESCRIPTION: SEQ ID NO:9:

TTAAAANNNN NNNNNYYYN 19

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="sequence"

(xi) SEQUENCE DESCRIPTION: SEQ ID NO:10:

TTAAAANNNN NNNNNNYYYN 20

(2) INFORMATION FOR SEQ ID NO:11:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="sequence"

(xi) SEQUENCE DESCRIPTION: SEQ ID NO:11:

TTTTNRRRN 9

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="sequence"

(xi) SEQUENCE DESCRIPTION: SEQ ID NO:12:

TTTTNNRRRN 10

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="sequence"

(xi) SEQUENCE DESCRIPTION: SEQ ID NO:13:

TTTTNNNRRR N                                                                                                    11

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:14:

TTTTNNNNRR RN                                                                                                   12

( 2 ) INFORMATION FOR SEQ ID NO:15:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:15:

TTTTNNNNNR RRN                                                                                                  13

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:16:

TTTTNNNNNN RRRN                                                                                                 14

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:17:

TTTTNNNNNN NRRRN                                                                                                15

( 2 ) INFORMATION FOR SEQ ID NO:18:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="sequence"

( x i ) SEQUENCE DESCRIPTION: SEQ ID NO:18:

TTTTNNNNNN NNRRRN				16

( 2 ) INFORMATION FOR SEQ ID NO:19:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="sequence"

( x i ) SEQUENCE DESCRIPTION: SEQ ID NO:19:

TTTTNNNNNN NNNRRRN				17

( 2 ) INFORMATION FOR SEQ ID NO:20:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="sequence"

( x i ) SEQUENCE DESCRIPTION: SEQ ID NO:20:

TTTTNNNNNN NNNNRRRN				18

( 2 ) INFORMATION FOR SEQ ID NO:21:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="sequence"

( x i ) SEQUENCE DESCRIPTION: SEQ ID NO:21:

ATKNNCNNYY NN				12

( 2 ) INFORMATION FOR SEQ ID NO:22:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="sequence"

( x i ) SEQUENCE DESCRIPTION: SEQ ID NO:22:

TTTTATTTGC CCCYC				15

SITE DIRECTED RECOMBINATION

This application claims the benefit of U.S. Provisional Application No. 60/003,063, filed Aug. 31, 1995.

BACKGROUND

Recombination has been a major tool in the field of molecular biology. The ability to introduce sequences into the genome of a cell has offered many opportunities in research and therapy. For the most part, random integration has been involved, where the DNA construct is randomly integrated throughout the genome. For many purposes, this is satisfactory, where one is interested in having the integrated DNA transcribed. Depending upon the purpose of the genetic modification and the nature of the cell, there have been various problems associated with the random approach. Frequently, expression is short lived, the cells providing transcription for only a relatively short period of time. Secondly, one can never be certain whether the site of integration is influencing the cellular phenotype, so as to change the cellular response to an imposed stimulus. Where one has provided DNA encoding a particular product of interest, in order to understand a particular pathway, there is the unfortunate uncertainty that one may have influenced the pathway by the site of integration, rather than the expression of the particular product. Also, the site of integration may result in a tumorigenic event, changing the character of the cell.

Because of the limitations of random integration, there have been numerous efforts to enhance the efficacy of homologous recombination. For the most part, these efforts have relied upon abilities to select for those cells which have undergone homologous recombination as compared to the much higher population of cells which have undergone random recombination. For example, one can have two markers, one where one positively selects, and the other where one negatively selects. Thus, one can select for cells which have undergone integration and lose the negative selection marker upon homologous recombination. Therefore, after selecting for the positive marker, one can then select against those cells which have undergone random integration and retain the negative marker.

Alternatively, one may use YACs or BACs, in which a particular gene is present. One can then modify the gene in yeast or baculovirus, where one obtains a much higher efficiency of homologous recombination. One can then return the large fragment to the original host with the modified gene. While the modification is at a site which is surrounded by normal flanking sequences, nevertheless, the site of integration of the large fragment is random and the large fragment may be fragmented during the integration. Therefore the result may be very complex and provide uncertainty about subsequent observations.

For many purposes, it will be desirable to be able to specifically integrate in a reproducible manner at a selected site. In this way, one can establish that the site does not interfere with other genes, that one can get stable transcription from the site, and that one may be able to compare results in different experiments with the assurance that the experiments are comparable, so far as the site of integration.

SUMMARY OF THE INVENTION

Enhanced efficiency and specificity of recombination is obtained by employing DNA constructs comprising a sequence hybridizing with a region of a vertebrate genome which endogenously undergoes a double stranded cut, which hybridizing sequence is joined to a sequence of interest. The consensus sequence is TTAAAA, where optionally one A or T may undergo a transition mutation followed by a sequence, where there preferred nucleotides at a number of sites. The construct may be used as single or double stranded DNA, RNA, circular or linear, and may have a second sequence for specific insertion at a single genomic site. The particular means used to introduce the DNA into the cell is not critical and may involve bare DNA, plasmids, viruses, or the like. The construct comprising the hybridizing sequence may also include one or more markers for selection.

DESCRIPTION OF THE SPECIFIC EMBODIMENTS

Methods and compositions are provided for targeted modification of genomic DNA using vectors comprising homology with a site subject to endogenous double stranded staggered restriction. The sequence defining the site is found in the genome at a plurality of sites, which serve as "hot spots" for integration of a sequence homologous to the sequence between the two nicks. The consensus-defined or conserved sequence is found to be associated with multicopy sequences, such as Alu, ID, B1, B2, etc., generally referred to as short interspersed repeated DNA elements ("SINEs"). The sequences are found to have a consensus hexanucleotide sequence TTAAAA, where the nick occurs with greater frequency between T and A, followed by a sequence which has a preference for particular nucleotides at a number of sites, the entire recombination sequence usually need not exceed 20 bases. The consensus sequence permits a transition mutation, C for T or G for A, particularly G for A. The nick in the other complementary strand occurs at least 5, more usually at least about 10 nucleotides from the other nick, occurring with highest frequency about 15 nucleotides from the nick in the first strand, so as to have most frequently a 15 base pair region flanked by nicks on opposite strands. However, the other nick may be as few as 5, usually 10 nt from the first nick or as many as 30 nt or more from the first nick. In addition, in many instances this double stranded cut will be associated with one of the SINEs. If one desires, one may use the consensus sequence of the SINE of interest as a second flanking sequence for recombination or a sequence proximal to the consensus sequence.

The presence of the nicks in the genomic DNA greatly enhances the efficiency of integration at sites where these nicks occur. The constructs which are employed may be single or double stranded DNA or RNA, usually as retrovital RNA, circular or linear and may provide for use of an Ω-vector or O-vector depending upon whether one wishes substitution or integration and the purpose of the particular construct. The construct will be referred to as the target-affined sequence, being capable of hybridizing, particularly being complementary to, the target DNA at the site between the nicks. The construct comprising the target-affined DNA may be introduced into the cell by any convenient means, depending upon the efficiency of the means, the environment in which the target-affined DNA comprising construct is to be introduced, and the like. Methods employed may be transfection, lipofection, liposomal fusion, including vital mediated fusion, electropotation, calcium precipitation, biolistics, or the like. Where retrovital RNA is used, the retroviral RNA or other nucleic acid construct may be packaged to enhance introduction into the cell. The retrovital RNA will usually be modified to reduce the probability of integration of the LTR, for example, by inactivating the endogenous integrase. To extend the period of time that the construct is present in the cell, one may use a plasmid, which may be stably or unstably maintained, e.g. inducibly maintained, in the cell.

The primary conserved consensus sequence on the first strand is 5'-TTAAAA-3', although one of the nucleotides may have a transition mutation, where T is substituted by C and A is substituted by G, followed by preferences at 3'-flanking nucleotides. The homologous sequence may extend beyond the nick and intrude into the double stranded portion by providing for nucleotides homologous to the nucleotides 5' of the nick site. Therefore, the flanking sequence homologous to the target sequence may be 3'-TTTT, 3'-ATTTT, or 3'-AATTTT, or the sequence having one transition mutation.

Besides the above indicated sequence, the nucleotides 3' of the sequence have certain preferences at certain positions. The conservation is not as strict as the site flanking the 5' nick site. The sequence will frequently come within the following sequence: TT↓AAAA(N)$_{0-10}$YYYN (SEQ ID NOS: 1–10), where N is any nucleotide, and Y is C or T, or the reciprocal sequence TTTT (N)$_{0-10}$RRRN (SEQ ID NOS: 11–20), where N is any nucleotide and R is G or A, there usually being not more than 1 mutation, particularly not more than one transition. The nicking site is indicated by the vertical inverted arrow.

In many instances the entire sequence at the 5' nick site, including the two nucleotides 5' of the nick site would come within the following sequence where in the case of two or more nucleotides being indicated, where the nucleotides are separated by a "\", the nucleotides to the left of the "\" have some preference over the nucleotides to the right of the "\". In addition, where N is indicated, that intends that there is not a strong preference at that site for any particular nucleotide. This is shown in Table 2 in the Experimental section. For the most part, the sequence will be as follows, beginning at the fifth nucleotide from the nick site: A T T/G T/N G/N C T/N C/N C/T C/T T/N C/N (SEQ ID NO:21). Sequences of particular interest will include at least the first 10 nucleotides of the above sequence or the complementary sequence, where there may be not more than 3 substitutions or mutations. A sequence of particular interest is TTTTATTTGCCCCT/CC (SEQ ID NO:22) or its complementary sequence with not more than 3 mutations, wherein T/C intends either nucleotide. These sequences will be outside the other functional sequences of the construct.

The approximate preferential order at each site will be as follows:

TABLE

| Position | Order of Preference |
|---|---|
| 5 | A T = G C |
| 6 | T C G A |
| 7 | T G = C A |
| 8 | T G = C A |
| 9 | G C = T A |
| 10 | C T G A |
| 11 | C T G A |
| 12 | C T G T |
| 13 | C T G = A |
| 14 | T = C G = A |
| 15 | C G = T = A |

For the most part, the nucleotides will be other than adenosine, primarily being cytosine or thymidine, where the thymidine has a greater incidence proximal to the nick position, while the cytosine has a greater incidence distal from the nicking position. The complementary sequence will have the reciprocal composition.

The subject invention may be used to enhance integration of a construct of interest, where there may be little preference for a particular or unique site for integration. Thus, by employing the consensus sequence as part of the construct, one will greatly enhance the efficiency of integration into a cellular host. This would be extremely important where the opportunity for selection of hosts into which the construct has integrated is weak or non-existent. In addition, there are a number of sequences which have been reported which fulfill the consensus sequence. If it is not important where such sequence is in the genome, or its position in the genome is known, then the particular known sequence may be used as the target site. Furthermore, where sequences are known where the consensus sequence is present, then the locus may be modified by providing a construct which comprises a sequence which is complementary to the sequence at the locus. In this way, sequences may be introduced, deleted, mutated, or any combination thereof. For example, one may exchange one transcriptional initiation region for another, introduce or remove an enhancer, replace one exon with another exon, delete a portion or all of a gene or a non-coding sequence, introduce a sequence which allows for specific recombination using an exogenous recombinase, introduce a sequence which will have an enhanced probability for double nicking, introduce a gene which allows for amplification, e.g. DHFR or metallothionein, or the like.

Alternatively, one may wish to have the construct integrate at one or a few different sites. This can be achieved by identifying the additional nucleotides between the nicks, as well as the nucleotides flanking the nicks. The additional nucleotides at the target site providing the target sequence between the nicks can be readily determined in a variety of ways. The various reported sequences associated with the consensus sequence, particularly as related to multicopy sequences, can be used for identifying a desired site for integration, where one would prepare the target-affined sequence so as to be homologous to the target sequence at the particular site. Alternatively, one may introduce DNA having the consensus sequence joined to a marker for selection. After introduction of the DNA and selection by means of the marker, one could identify the region into which the construct has integrated and determine its sequence. By restricting the genome, one could identify fragments of different sizes in which the marker has become integrated and sequence the regions flanking the marker. These regions could then be used as primers using PCR to obtain the site at which the construct integrated and identify the particular overhang resulting from the nicks. In this way, one would not only identify consensus sequence regions associated with SINEs, but also other proximal regions identified with sequences other than SINEs.

By employing known sequences, and by investigating for new sequences, one can build up a library of sequences which will identify "hot spots" for integration throughout the genome of the host. By identifying introns as sites for integration, one may influence the nature and regulation of expression of specific genes associated with a particular intron.

In some instances, one may wish to introduce the particular construct at the integration site by using alternative techniques of homologous recombination. These techniques include in-out techniques, where one uses a combination of positive and negative selection markers (Valancious and Smithies, *Mol. Cell Biol.* (1991) 11: 1402–1408). One would have a negative selection marker outside of the region of interest and the target-affined region, so that upon recombination at the site of homology, the negative marker would be lost. One would then select for cells lacking the negative marker, where those cells comprising the negative marker would be killed. One may use RecA coated DNA, either a single strand or complementary strands to further enhance integration at the target site. Other techniques may also be applicable.

The double stranded nicks are found in the eukaryotic kingdom, particularly vertebrates, more particularly mammalian cells. Hosts of particular interest include laboratory animals, e.g. rodents, lagomorpha, etc., domestic animals, such as canine, feline, bovine, equine, porcine, and the like; as well as primates, including monkeys, gorillas, humans, and the like.

The constructs may take many forms, where the target-affined sequence may be joined to a variety of other sequences for a variety of purposes. The construct will have the consensus sequence, which will normally be at least 4 nt, more usually at least 8 nt, preferably at least 10 nt, and frequently 15 nt or more, generally not more than about 30 nt, usually not more than about 20 nt. By consensus sequence is intended the sequence between the nicks. However, additional homologous or complementary sequence may be employed to enhance specificity. Joined to the consensus sequence will be one or more sequences of interest, which may be coding or non-coding, so as to code for a peptide of interest, an antisense sequence, a regulatory sequence, or the like. The sequence of interest will not be found in proximity ($\leq 10$ kb) to the consensus sequence in the genome of the target cell host. The target-affined sequence will be able to hybridize with the sequence between the nicks on the complementary strands. The construct may or may not include a second sequence homologous to a sequence in the target region. By having a second sequence homologous to a sequence in the target region, the efficiency of integration as well as the specificity can be enhanced. If desired, the termini of a dsDNA construct may be complementary to the complementary sequences between the nicks. In this was the construct may be inserted into the region between the nicks.

The term homology is used to indicate a likeness of structure and conservation of biological function. Calculations of nucleic acid or amino acid sequence identity, as described below, provide a convenient method of identifying homologous or related genes, herein "homologs". Such homologs may be members of a gene family present in the same genome, or may be corresponding genes from different species. Mammalian homologs have substantial sequence similarity to the subject sequences, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, and include BLAST, described in Altschul et al. (1990) *J Mol Biol* 215: 403–10; ADVANCE and ADAM, described in Torelli and Robotti (1994) *Comput Appl Biosci* 10: 3–5; and FASTA, described in Pearson and Lipman (1988) *P.N.A.S.* 85: 2444–8.

Nucleic acids having sequence similarity are detected by hybridization under low stringency conditions, for example, at 50° C and 10XSSC (0.9M saline/0.09M sodium citrate) and remain bound when subjected to washing at 55° C in 1XSSC.

A transcription cassette will comprise in the direction of transcription, a transcription initiation regulatory region, which will include the promoter and may include one or more enhancers, the sequence of interest under the transcriptional regulation of the initiation regulatory region, and a transcriptional termination regulatory region, which will usually include a polyadenylation signal. Associated with the transcriptional regulatory sequences for genes to be expressed will be the appropriate translational regulatory sequences. Connected with the sequence of interest may be a marker, which allows for selection of cellular hosts comprising the construct. The marker may provide for resistance to an antibiotic or toxin, e.g. resistance to G418, chloramphenicol, tetracycline, gancyclovir, etc., may provide prototropy to an auxotrophic host, e.g. complementation of a mutation resulting in a metabolic requirement, providing a detectable signal, e.g. an enzyme capable of providing a colored, fluorescent or luminescent product from a substrate, or the like. Usually, only one marker will be used, but 2 markers or even more, may find application. In addition one may have other genetic information, such as an origin of replication, restriction site or polylinkers, primer sites, particularly for amplification by PCR, transposase sites for integration, vital packaging signals for packaging in a capsid or envelope, genes capable of amplification, e.g. DHFR, metallothionein, etc., or the like.

One can provide for expression of a protein of interest. The protein may be involved with various metabolic pathways in the cell, may be secreted, so as to affect other cells, may be associated with intracellular regulation, may change the phenotype of the cells, or the like. Alternatively, one can provide for the transcription of antisense sequences, which may inhibit the expression of various proteins. Thus, the subject invention may be used in a variety of ways. One may introduce genes for expression of proteins to isolate the proteins and use them for various purposes, such as therapeutic purposes. Such proteins include erythropoietin, blood factors, such as Factors V to XII, complement proteins, serum albumin, cytolkines, such as interleukins 1 to 16, colony stimulating factors, such as G, M and GM, hormones, such as insulin, growth hormone, interferons, $-\alpha$, $-\beta$, and $-\gamma$, growth factors, e.g. epidermal growth factor, platelet derived growth factor, neuronal growth factor, etc., other growth factors, such as tumor necrosis factor, transcription factors, stem cell factors, such as cyclins and kinases, enzymes, surface membrane receptors, immunoglobulins, major histocompatibility complex proteins, soluble or surface bound, apolipoproteins, proteins associated with apoptosis, e.g. FAS, housekeeping proteins, structural proteins, DNA binding proteins, and the like.

One may introduce genes to provide for expression of particular receptors in cells capable of being maintained in culture, e.g. stable strains, whereby the cells may then be used for screening various compounds for binding to the receptor. Receptors of interest include receptors which bind to the factors indicated above, T cell receptor proteins, CD4, -8, -69, and the like.

One may introduce genes which allow for secretion of the protein, where by appropriate choice of the cell, the secreted protein will be in the proper conformation and appropriately processed, e.g. glycosylation, methylation, acylation, and the like. One may provide for various signal sequences in the expressed protein, for secretion, phosphoinositol substitution, farnesylation, prenylation, etc.

If desired, one may use a variety of enhancers, which may be cell specific so that the subject constructs will only function in cells of a particular type. For example, one may provide for an enhancer which is specific to myoblasts, prostate cells, muscle cells, hematopoietic cells, such as lymphocytes, osteoclasts, macrophages, megakaryocytes, erythrocytes, mononuclear cells, and the like; keratocytes; neuronal cells, glial cells, Schwann cells, astrocytes, oligodendrocytes, ganglions, etc.; epithelial cells, endothelial cells, synovial cells, or the like. A wide variety of promoters and enhancers are known and may be used in conventional ways associated with integration into the genome.

Thus, one may provide for modification of cells, particularly for cells used in culture for producing products, screening products, investigating metabolic pathways, and the like. One may also modify animals to produce transgenic animals, by correcting defects, introducing defects, such as dominant negative genes, where expression may be constitutive or induced, providing for new capabilities, such as the production of exogenous proteins, which may provide protection from various stresses, improve metabolic response, enhance or diminish susceptibility to diseases, such as cancer, autoimmune diseases, etc.

Alternatively, one may provide for the production of an antisense sequence, so as to inhibit the transcription or expression of various products encoded by a gene. This may be used to investigate metabolic pathways, effect on phenotype, effect on response to various agents, and the like. The technique may also be used for producing transgenic animals, whereby one wishes to be able to control the expression of a particular product to determine its effect on phenotype. Transcription of the antisense sequence may be constitutive or induced.

One may introduce various sequences which allow for specific insertion at the site in the presence of a particular recombinase. Thus, sequences such as the cre/lox, AC/DC, or the consensus sequence, particularly as a tandem multicopy sequence may be introduced, where by introducing various constructs having specific consensus sequences associated with the sequences recognized by the recombinase, one can provide for insertion and excision of the particular sequence. This approach may have application where one may wish to introduce at a single site associated with a particular gene a variety of sequences to determine the effect of variation in sequence or to provide cells, where one can introduce sequences at a defined site.

To recapitulate, the subject compositions may find use in modifying the phenotype of cells for use in culture for producing products, for investigating the response of receptors, for investigating metabolic pathways, for investigating expression products involved in regulation of transcription or transduction of signals, and the like. The subject compositions may also be used for the production of transgenic animals by providing for novel capabilities to the cells or inhibiting endogenous capabilities, for production of protein products, to investigate physiological indications and screening cosmetics, foods and drugs, and the like. By using antisense sequences, one can effectively inhibit both copies of a gene, so as to ensure the substantial absence of the particular transcriptional or translational product. In addition, one may use the subject methodology for enhancing efficiency in gene therapy, where one wishes to provide for a capability in which the host is deficient. Thus, by introducing a wild type gene into cells which have a mutant gene, one may provide for the function of the wild type gene. Alternatively, one may provide for secretory products, where the cells do not naturally secrete the product, but can provide the product to the vasculature.

The construct may be provided as circular DNA, where the two strands are hybridized, but have nicks at different places so that if linear, the staggered ends would be homologous. To inhibit oligomerization of the dsDNA, one could extend one of the strands with a non-homologous sequence to extend past the other strand. Usually, such extension would not exceed about 10 nt.

Alternatively, one may provide for linear DNA which is staggered or blunt ended, where each of the ends has a sequence which is homologous to a sequence at the target. The sequences homologous to the target may be the same (including complementary) or different. Since there is the possibility of looping out after the integration and loosing the sequence of interest, where one has the same or substantially the same sequences for integration, the stability of integration would have to be determined on a case by case basis. By determining the sequence at the site of interest, one may provide for homology at the target sequence where the regions of homology to the target sequence at opposite ends of the double stranded DNA are not homologous to each other. Alternatively, one may use single stranded DNA to avoid the problems associated with double stranded DNA. However, double stranded DNA will be more stable intracellularly and, therefore, may find application in a number of situations where stability is important.

For delivering the DNA, various constructs may be employed, where the gene is bare DNA, is part of a plasmid or a virus, or an expression cassette, optionally joined to a marker. Various viruses can be used for introduction of constructs into mammalian cells, such as adenovirus, papilloma virus, and the like, episomal elements, e.g. plasmids, and the like. The DNA may be packaged in a capsid or envelope, a liposome, or the like The following examples are offered by way of illustration and not by way of limitation.

EXPERIMENTAL

The basic analysis was performed on sequences flanking human Alu and rodent ID retroposons, which are available in statistically significant numbers. GenBank coordinates of unique Alu elements were obtained from RepBase and coordinates of ID sequences were directly identified in GenBank using CENSOR program. Pairs of sequences flanking individual Alu and ID retroposons, approximately 50 bp long, were extracted and aligned against each other using Smith-Waterman algorithm. Based on the alignment, only identical subsequences, at least 10 bp long, were selected. If the 5' subsequence in each pair was not immediately adjacent to the 5' end of complete Alu or ID sequences the pair was eliminated from the set. The remaining fragments were considered to be a representative set of flanking repeats.

The 5' flanking repeats were left-adjusted so that they all started at the same position. Similarly, the 3' repeats were right-adjusted so that they all ended at the same position. The flanking repeats were extended by an additional 15 bp away from the retroposon location and the extensions are referred to as 5' and 3' adjacent sequences.

The overall base compositions of the flanking repeats as well as of the adjacent sequences are shown in Table 1. The data confirms that the flanking repeats are adenine-enriched, primarily at the expense of pyrimidines when compared with adjacent regions. The 3' adjacent sequences show some elevation of the guanine content relative to the 5' adjacent sequences and flanking repeats.

TABLE 1

| | Alu | | | | ID | | | |
|---|---|---|---|---|---|---|---|---|
| | T | C | A | G | T | C | A | G |
| 5'-adj | 33.7 | 19.5 | 30.3 | 16.5 | 32.2 | 21.4 | 31.5 | 14.9 |
| Fl. repeats | 18.5 | 11.0 | 54.9 | 15.6 | 23.4 | 11.1 | 48.4 | 17.1 |
| 3'-adj | 24.0 | 18.8 | 35.8 | 21.5 | 28.9 | 16.8 | 29.5 | 24.8 |

Base compositions at individual positions of 5' flanking repeats and of adjacent sequences are listed in Table 2, and analogous data for 3' flanking repeats and their adjacent regions are listed in Table 3.

Using base composition from Table 1, one can calculate expected uniform distribution of bases at each position. The expected values for the maximal number of observed sequences in each group (i.e.: 104 Alu, and 54 ID), are listed as Exp. (top) and Exp. (bot.) in the middle of Tables 2 and 3.

TABLE 2

| | | Alu | | | | | ID | | | |
|---|---|---|---|---|---|---|---|---|---|---|
| No. | P | T | C | A | G | P | T | C | A | G |
| -15 | A | 31 | 20 | 34 | 19 | A | 14 | 9 | 20 | 11 |
| -14 | A* | 23 | 15 | 36 | 30 | C | 16 | 21 | 11 | 6 |
| -13 | A* | 19 | 22 | 46 | 17 | C* | 10 | 23 | 15 | 6 |
| -12 | A | 25 | 21 | 45 | 13 | A | 11 | 11 | 25 | 7 |
| -11 | A | 27 | 24 | 30 | 24 | A* | 9 | 4 | 30 | 11 |
| -10 | A | 27 | 21 | 39 | 17 | A | 13 | 10 | 23 | 8 |
| -9 | T | 34 | 28 | 28 | 14 | T | 21 | 12 | 14 | 7 |
| -8 | T | 32 | 26 | 30 | 16 | A | 14 | 9 | 19 | 12 |
| -7 | T | 36 | 22 | 28 | 18 | A | 10 | 14 | 20 | 10 |
| -6 | T | 37 | 16 | 33 | 18 | A | 11 | 16 | 17 | 10 |
| -5 | T | 41 | 20 | 31 | 12 | T | 20 | 11 | 13 | 10 |
| -4 | T | 32 | 26 | 27 | 19 | T | 21 | 13 | 16 | 4 |
| -3 | T | 37 | 18 | 31 | 18 | T | 20 | 9 | 17 | 8 |
| -2 | T* | 71 | 7 | 14 | 12 | T* | 38 | 2 | 6 | 8 |
| -1 | T* | 55 | 16 | 23 | 10 | T* | 33 | 9 | 9 | 3 |
| Exp. (top) | | 35.0 | 20.3 | 31.5 | 17.2 | | 17.4 | 11.6 | 17.0 | 8.0 |
| Exp. (bot.) | | 19.2 | 11.4 | 57.1 | 16.2 | | 12.6 | 6.0 | 26.1 | 9.2 |
| 1 | A* | 13 | 1 | 83 | 7 | A* | 2 | 0 | 50 | 2 |
| 2 | A* | 5 | 1 | 76 | 22 | A* | 1 | 0 | 45 | 8 |
| 3 | A* | 6 | 1 | 84 | 13 | A* | 1 | 1 | 40 | 12 |
| 4 | A* | 6 | 0 | 84 | 14 | A* | 2 | 0 | 44 | 8 |
| 5 | A | 16 | 4 | 69 | 15 | A | 9 | 5 | 34 | 6 |
| 6 | A | 28 | 15 | 45 | 16 | T | 21 | 8 | 18 | 7 |
| 7 | T* | 34 | 19 | 31 | 20 | A | 16 | 6 | 19 | 13 |
| 8 | A | 24 | 13 | 46 | 21 | A | 15 | 6 | 23 | 10 |
| 9 | A | 21 | 12 | 53 | 18 | A | 11 | 6 | 24 | 13 |
| 10 | A | 22 | 17 | 48 | 17 | T | 19 | 10 | 14 | 11 |
| 11 | A* | 21 | 18 | 32 | 21 | T* | 15 | 13 | 15 | 7 |
| 12 | A | 22 | 17 | 37 | 10 | T | 16 | 9 | 14 | 9 |
| 13 | A | 17 | 15 | 41 | 6 | T | 16 | 9 | 11 | 10 |
| 14 | A | 15 | 13 | 30 | 8 | T | 17 | 5 | 13 | 7 |
| 15 | A | 13 | 9 | 26 | 11 | A | 4 | 9 | 11 | 8 |
| 16 | A | 10 | 8 | 13 | 14 | T | 8 | 2 | 5 | 2 |
| 17 | A | 3 | 2 | 6 | 6 | T | 5 | 1 | 4 | 1 |
| 18 | A | 0 | 0 | 5 | 2 | A | 3 | 0 | 4 | 1 |

All flanking repeats start at position 1; regions 5' adjacent to the flanking repeats are indicated by negative numbers (column 1). Columns 2-11 show predominant bases (P) and frequencies of T, C, A, and G at the corresponding positions in Alu and ID flanking repeats. Exp. (top) and Exp. (bot.) indicate expected frequencies for the top and the first 10 positions of the bottom part of the table, respectively.

TABLE 3

| | | Alu | | | | | ID | | | |
|---|---|---|---|---|---|---|---|---|---|---|
| No. | P | T | C | A | G | P | T | C | A | G |
| -20 | A | 0 | 0 | 3 | 2 | A | 2 | 0 | 5 | 0 |
| -19 | A | 0 | 0 | 9 | 0 | A | 0 | 0 | 6 | 1 |

TABLE 3-continued

| | | | | | | | | | |
|---|---|---|---|---|---|---|---|---|---|
| -18 | A | 1 | 2 | 17 | 0 | A | 0 | 0 | 9 | 0 |
| -17 | A* | 5 | 0 | 33 | 5 | A | 0 | 0 | 10 | 2 |
| -16 | A* | 7 | 0 | 79 | 7 | A | 2 | 1 | 15 | 2 |
| -15 | A* | 8 | 2 | 118 | 17 | A* | 1 | 0 | 32 | 4 |
| -14 | A* | 11 | 2 | 135 | 28 | A* | 2 | 0 | 44 | 5 |
| -13 | A* | 18 | 3 | 166 | 26 | A* | 2 | 0 | 38 | 15 |
| -12 | A* | 38 | 7 | 188 | 24 | A* | 7 | 1 | 46 | 6 |
| -11 | A* | 53 | 15 | 187 | 39 | A | 8 | 4 | 41 | 10 |
| -10 | A | 69 | 38 | 170 | 52 | A | 15 | 9 | 25 | 18 |
| -9 | A | 58 | 45 | 162 | 64 | A | 19 | 11 | 25 | 12 |
| -8 | A | 69 | 49 | 139 | 72 | A | 21 | 8 | 24 | 14 |
| -7 | A* | 68 | 66 | 138 | 57 | A | 11 | 8 | 36 | 12 |
| -6 | A | 91 | 46 | 134 | 58 | A | 17 | 11 | 28 | 11 |
| -5 | A | 83 | 55 | 138 | 53 | A | 17 | 11 | 20 | 19 |
| -4 | A* | 113 | 48 | 116 | 52 | T* | 33 | 6 | 19 | 9 |
| -3 | T* | 106 | 74 | 89 | 60 | C* | 14 | 20 | 17 | 16 |
| -2 | T* | 120 | 81 | 67 | 61 | T* | 23 | 18 | 16 | 10 |
| -1 | A* | 91 | 50 | 117 | 71 | T | 23 | 9 | 20 | 15 |
| Exp. (top) | | 73.0 | 42.1 | 159.6 | 54.3 | | 14.4 | 7.6 | 32.8 | 12.2 |
| Exp. (bot.) | | 86.8 | 61.4 | 107.6 | 69.2 | | 17.8 | 12.3 | 20.1 | 16.8 |
| 1 | A* | 59 | 47 | 135 | 84 | A | 15 | 6 | 26 | 18 |
| 2 | A* | 90 | 42 | 143 | 49 | A | 17 | 12 | 27 | 9 |
| 3 | A | 70 | 62 | 108 | 82 | A | 14 | 12 | 19 | 19 |
| 4 | A | 89 | 60 | 107 | 63 | G | 17 | 9 | 18 | 19 |
| 5 | A | 87 | 55 | 103 | 73 | A | 17 | 12 | 19 | 14 |
| 6 | T | 101 | 64 | 87 | 65 | G | 17 | 8 | 18 | 19 |
| 7 | A | 92 | 54 | 100 | 71 | G | 15 | 12 | 16 | 19 |
| 8 | A | 88 | 71 | 96 | 61 | A | 16 | 9 | 21 | 16 |
| 9 | A | 82 | 72 | 96 | 64 | T | 24 | 9 | 17 | 12 |
| 10 | A | 80 | 56 | 109 | 69 | C | 11 | 18 | 17 | 16 |
| 11 | A | 81 | 74 | 86 | 73 | T | 19 | 15 | 14 | 14 |
| 12 | A | 88 | 62 | 101 | 62 | G | 17 | 16 | 11 | 18 |
| 13 | A | 84 | 62 | 106 | 62 | T | 19 | 12 | 19 | 12 |
| 14 | T | 92 | 65 | 92 | 65 | A | 18 | 8 | 19 | 17 |
| 15 | A | 87 | 51 | 106 | 69 | A | 14 | 14 | 21 | 13 |

Flanking repeats are 3' adjusted and numbered by negative numbers with their ends at positions -1; regions downstream from the flanking repeats start at position 1 (column 1). Columns 2-11 show predominant bases (P) and frequencies of T, C, A and G at the corresponding positions in Alu and ID flanking repeats. Exp. (top) indicate expected frequencies for positions -1 through -10 and Exp. (Bot.) Indicated expected frequencies for positions 1-15.

The strong non-randomness around the first nicking site is reflected in the distribution of hexanucleotides which include two bases preceding and four bases following the 5' nicking site as shown in Table 4. The most abundant is TT AAAA and its variants differing by one transition-type mutation (i.e.: A<->G or T<->C substitution), with the exception of "AAAAAA".

TABLE 4

| Frequency | Hexamer(s) |
|---|---|
| 18 | TTAAAA |
| 14 | TTAGAA, TTAAGA |
| 9 | TCAAAA, AAAAAA |
| 8 | TTAAAG |
| 5 | TTGAAA |
| 4 | TTTAAA, TCAAGA, GAAAAA |
| 3 | TCTAAA, CTAAAA |
| 2 | TGAAAA, TCAGAA, TAAGAA, TAAAAA, GTGAAA, GTAGAA, GTAAAA, CTAAAG, CAAAAA |
| 1 | TTTGAT, TTATTA, TTATAA, TTAGGA, TTAGAG, TTACAA, TTAATT, TTAACA, TTAAAT, TGTTCA, TGAGAA, TGAAAT, TGAAAG, TCAAAT, TATTAA, TATAAA, TAGAAG, TAATAA, TAAGGA, TAAGAG, TAAATG, TAAAAG, GTTAAA, GTAAGT, GTAAGA, GTAAAG, GGAGGA, GGAAAA, GCAGAA, GCAAGA, GCAAAA, GAAAAG, CCAATA, CCAAAA, ATAAAT, AGTTTT, AGCATA, AGAGAA, AGAAAG, AGAAAA, ACTAAA, AATAAG, AAGGGG, AAAATA, AAAAAG |

The nonrandom distribution of different bases around both ends of the flanking repeats is a signal for an endonucleolytic enzyme involved in generating the double stranded breaks. The second strand breaks within a variable distance from the first one which translates into variable lengths of flanking repeats. The minimum distance between the nicks could not be determined with any certainty since the shorter the flanking repeats, the more difficult it is to distinguish them from random oligonucleotides happening to match each other at both sides of the retroposon. On the other hand, the preferred maximum distance appears to be 15 bp, although flanking repeats twice as long could also be observed. As can be seen from the bottom part of Table 2, the total numbers of Alu flanking repeats 16, 17 and 18 bp long are 35, 17 and 7, respectively. The decline in numbers of shorter flanking repeats (11–15 bp long), is much less steep as the corresponding numbers are 92, 86, 82, 66 and 57. A similar rule applies to direct repeats flanking ID retroposons.

It is evident from the above results that there are a broad range of sites where double strand breaks are being introduced by an endogenous endonuclease, which combined with a recombination process can be used for efficient targeting of extrachromosomal DNA to predetermined chromosoma/sites. This allows for specific targeting to particular silos in the genome so as to provide for stable integration and reproducible transcription from the site. In this way, one can minimize influences resulting from random integration of sequences, where the site of integration can substantially effect the stability and level of transcription over time.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for integrating a DNA sequence of interest into the genome of an isolated vertebrate host cell, said method comprising:

introducing a DNA construct into said isolated vertebrate host cell, wherein said construct comprises the DNA sequence of interest and a sequence homologous to a consensus-defined recombination region of a vertebrate cell, said homologous sequence comprising at least the first and last four nucleotides of the sequence AAAA (N)$_{0-10}$YYYN (SEQ ID NOS: 1–10) or its complementary sequence with not more than one mutation, said mutation being in the first four nucleotides, and wherein N is any nucleotide and Y is C or T, such that the DNA sequence of interest is integrated into the genome of said isolated vertebrate host cell.

2. The method according to claim 1, wherein said construct is introduced as single stranded DNA.

3. The method according to claim 1, wherein said construct is introduced as double stranded DNA.

4. A method for integrating a DNA sequence of interest into the genome of an isolated vertebrate host cell, said method comprising:

introducing a DNA construct into said isolated vertebrate host cell, wherein said construct comprises (1) a recombination region homologous to a consensus-defined flanking region of a short interspersed repeated DNA element (SINE) joined to (2) a transcriptional cassette as said sequence of interest; and (3) a marker for selection of cells comprising said construct, such that the DNA sequence of interest is integrated into the genome of said isolated vertebrate host cell.

5. The method according to claim 4, wherein said isolated vertebrate host cell is a mammalian host cell.

6. The method according to claim 4, wherein said recombination region comprises TTTT or its complementary sequence.

7. The method according to claim 4, wherein said sequence comprises at least the first and last four nucleotides of the sequence $AAAA(N)_{0-10}YYYN$ (SEQ ID NOS: 11–20) or its complementary sequence with not more than one mutation, said mutation being in the first four nucleotides, and wherein N is any nucleotide and Y is C or T.

8. The method according to claim 4, wherein said construct is introduced as single stranded DNA.

9. The method according to claim 4, wherein said construct is introduced as double stranded DNA.

10. The method according to claim 6, wherein said TTTT is preceded by AA.

11. The method according to claim 10, wherein said recombination region is complementary to an Alu or ID flanking region.

12. A DNA sequence comprising a transcriptional cassette and a sequence homologous to a consensus-defined recombination region of a vertebrate host cell, said sequence comprising at least the first and last four nucleotides of the sequence $AAAA(N)_{0-10}YYYN$ (SEQ ID NOS: 11–20) or its complementary sequence with not more than one mutation, said mutation being in the first four nucleotides, and wherein N is any nucleotide and Y is C or T.

13. The DNA sequence according to claim 12, further comprising a marker for selection in a vertebrate host cell.

14. The DNA sequence according to claim 12, further comprising a viral sequence for packaging.

15. The DNA sequence according to claim 12, wherein said transcription cassette comprises a coding region.

16. The DNA sequence according to claim 12, wherein said transcription cassette comprises an antisense sequence.

17. The DNA sequence according to claim 12, wherein said consensus-defined recombination region sequence is a SINE flanking sequence.

* * * * *

UNITED STATES PATENT AND TRADEMARK OFFICE
CERTIFICATE OF CORRECTION

PATENT NO. : 5,695,977

DATED : December 9, 1997

INVENTOR(S) : JURKA

It is certified that error appears in the above-identified patent and that said Letters Patent is hereby corrected as shown below:

Column 1, in a new paragraph immediately preceding "BACKGROUND", insert --This was made with Government support under grant number DE-FG03-95ER62139 awarded by the Department of Energy. The Government has certain rights in this invention.--

Signed and Sealed this

Tenth Day of February, 1998

Attest:

BRUCE LEHMAN

*Attesting Officer*     *Commissioner of Patents and Trademarks*